United States Patent [19]

Schlossman

[11] Patent Number: 5,356,617

[45] Date of Patent: Oct. 18, 1994

[54] PIGMENT-MATERIAL-MICROSPHERE COMPLEXES AND THEIR PRODUCTION

[75] Inventor: David S. Schlossman, W. Orange, N.J.

[73] Assignee: Kobo Products, Inc., South Plainfield, N.J.

[21] Appl. No.: 986,260

[22] Filed: Dec. 7, 1992

Related U.S. Application Data

[63] Continuation-in-part of Ser. No. 523,315, May 14, 1990, Pat. No. 5,314,683.

[51] Int. Cl.$^5$ ...................... A61K 7/021; A61K 7/035
[52] U.S. Cl. ......................... 424/63; 424/64; 424/69; 424/78.03; 424/401; 428/403; 428/404; 514/770; 514/772.3; 514/844
[58] Field of Search ..................... 424/490, 63, 64, 401

[56] References Cited

U.S. PATENT DOCUMENTS 4,756,906 7/1988 Sweeny ................................. 424/63

Primary Examiner—Thurman K. Page
Assistant Examiner—James M. Spear
Attorney, Agent, or Firm—Handal & Morofsky

[57] ABSTRACT

New cosmetic raw materials are provided in the form of complexes of pigment materials coupled to small microspheres providing complexes that impart richness and feel, with low oil absorbency while displaying the optical and other properties of the pigment. Improvements in spatial disposition of small pigment particles provide a better dispersion of pigment in and products such as makeups, creams, lipsticks, blushers, nail enamels, and the like. Preferred embodiments include talc, nylon, silica, starches and iron oxide pigments coupled by a liquid titanate coupling agent to microspheres of polyvinylidene chloride copolymer, polyethylene, nylon and silica. Simple methods of manufacture include spraying a liquid titanate in solution on a blended mixture of pigment and microsphere and drying the product while blending, to cure it.

20 Claims, 9 Drawing Sheets

PIGMENT-MATERIAL-MICROSPHERE COMPLEXES AND THEIR PRODUCTION

CROSS-REFERENCE TO A RELATED APPLICATION

This application is a continuation-in-part of my co-pending U.S. patent application Ser. No. 07/523,315, filed May 14, 1990 now U.S. Pat. No. 5,314,683 and entitled "Method of Coupling Cosmetic Materials and Cosmetics Containing Coupled Materials".

TECHNICAL FIELD

The present invention relates to new cosmetic raw materials in the form of novel complexes of microspheres with cosmetic materials and the manufacture of such raw materials. The new complexes impart unique and desirable characteristics to cosmetic end-product formulations in which they are employed as ingredients. The invention can utilize either organic or inorganic microspheres.

BACKGROUND

Since prehistoric times, when body paint was first being applied, separation of pigments and other components in paints and dyes has led to inconsistent colors and non-uniform applications of make-up. Separation and settling is a well-known phenomenon in liquid, or fluid-phase systems, that results in diminished shelf-life, non-uniform colors and ineffectual application of make-up. Separation can also take place in powder mixtures with the less dense material tending to concentrate in the upper volume of the mixture.

Advances in the cosmetic arts, and the choice of possible cosmetic formulants, are constrained and delimited by, among others, the following requirements:
  compatibility, both physical and chemical, with customary cosmetic formulants and pre-cursor materials which can include both hydrophilic and lipophilic materials;
  stability, again both physical and chemical and also biological, in end-product formulations for extended distribution and shelf-life, especially against settling, loss of volume and spoilage;
  end-product stability for the consumer after opening;
  end-use functionality which, in addition to the more or less subtle ornamental functions required of, for example, lipstick, mascara, face powder and nail polish, includes the more elusive qualities of feel, ease of application as well as an appropriate range of adhesion; and, most importantly,
  non-toxicity, non-comedogenicity, hypoallergenicity and the like, in other words, dermatological innocuity.

Many, but not all, of these properties can be related to dispersibility of the pigment materials and the art is replete with proposals for improving pigment dispersibility. Noting that a pigment can be considered as a concentrated particle of colorant or other material providing a useful visual effect, including pigment extending, techniques to improve dispersibility usually comprise grinding or milling pigment materials to a fine particle size and coating the particles.

Milling of course increases the available surface area and visual effect of the pigment, and thus its effectiveness. There are many prior art teachings relating to the coating of pigment materials to improve their dispersibility. Most pigment materials tend to have a hydrophilic surface character making them hard to disperse in organic media, and it is accordingly well-known to treat pigment materials to give them a hydrophobic character and to use surfactants, anti-flocculants and the like to improve the dispersibility of the pigment materials.

The present invention takes a new approach to the improvement of dispersibility, providing striking results of great value to the cosmetics industry. Indeed the invention succeeds in providing some control over the spatial distribution of particulate pigment materials in subsequent cosmetic formulations.

In U.S. Pat. No. 4,877,604 to M. Schlossman there are described a number of methods to coat pigments and pigment materials with titanate coupling agents including isopropyl triisostearoyl titanate. M. Schlossman provides valuable improvements in the art of pigment material dispersibility.

In a different industry, with different constraints, the plastics industry, materials known as spherical polymeric particulates in powder form and hollow spheres in powder form, either of which materials may be called microspheres, are known as valuable fillers and are prized for their sphericity, controlled particle size and low density, see for example, Ruhno "Handbook of fillers for plastics", edited by H. S. Katz et al , pp. 437–438 Van Nostrand Reinhold (1978).

According to Ruhno, there are major advantages to the plastics industry in the ability of microspheres to act as fillers in composite materials, displacing high-priced polymers with lower density, and better density control than solid mineral fillers. Some end product advantages are uniform shrinkage, improved sandability and increased impact resistance.

A brief review of the history and development of spherical polymeric powders or microspheres, including hollow spheres, sized under 1000 micron, can be found in the Ruhno reference. Inorganic and organic hollow spheres are described and referred to as "microspheres" the term being used for materials which are spherical, small and light, and in the context of this reference, hollow and polymeric. Obviously, the above-described end-product advantages are not of general use in cosmetics.

Native organic polymeric microspheres have been incorporated in cosmetic compositions to impart desirable texture characteristics of smoothness and feel, as well as pourability to powder cosmetics, notably makeup, see for example UK Patent Application GB 2 191 945. An important drawback is high oil absorption causing excessive drying and caking. Another problem is that small round microspheres do not adhere well to the skin.

Inert microspherical materials, especially organic polymeric materials, for example spherical nylon or polyethylene powder, have been employed as a cosmetic raw material, see for example, the Journal of The Society of Cosmetic Chemists, 41, 197-207, May/June 1990 ("Cosm. Chem." hereinafter). Here, hybridized powders are disclosed in which fine-chemical deodorant powders, specifically zinc oxide and aluminum chlorhydrate are mechanically layered on such microspheres by mixing and percussion in a centrifugal ball mill. The active, chemical quenching power of the deodorants is retained and improved physical properties of the deodorant powders result, including better texture and lower coefficients of kinetic friction, the latter correlating with smoothness.

Mechanofusion processes are expensive and difficult to use on a commercial scale for bulk raw materials. A drawback of such cosmetics-containing microspherical particles produced by mechanofusion processes, especially organic polymeric particles, is that they can have too high an oil absorption capacity, giving an unacceptable drying effect to the skin. Furthermore, the mechanical layering technique results in the outer powders being partially buried, reducing their exposed surface area, a drawback for pigment materials. Another difficulty may arise during pulverization when too much heat can cause polymeric microspheres to melt.

Also, while deodorants may be embraced by some interpretations of the term "cosmetic" their properties are obviously not those required for decorative cosmetics as a material used to adorn embellish or beautify the wearer, to enhance the visible appearance of exposed surfaces of the wearer, and they are not usually applied to normally exposed skin surfaces.

The Cosm. Chem. disclosure is silent as to the suitability of small inert spherical powders for inclusion in appearance-enhancing cosmetics, especially for topical application where the oil absorption and light-reflective properties of cosmetics are paramount. Nor is the Cosm. Chem. disclosure relevant to liquid phase dispersions for manual application by spreading. Certain additional properties are vital for appearance-enhancing cosmetics. These properties include not only their appearance and their ability to sustain and develop pigments, but also end-product characteristics such as spreadability.

Additionally, while the physical properties of feel and smoothness that can be contributed by microspheres in some formulations may be desirable out of the container, these are of no value if the product lacks adequate adhesion to remain on the skin. This is a further drawback of microspheres.

Broad usage of microspheres is contraindicated by high cost in addition to technical factors. Formulators may encounter difficulties during processing, for example, blending inconsistencies arising from bulk density differences; pressing problems in which oil can come out, and stability problems because prolonged oil absorption can cause dried cake, cracking, and impair the texture of the product. In addition, smooth, round particles do not adhere well to the skin.

SUMMARY OF THE INVENTION

This invention solves a problem. One of the problems it solves is the provision of an improved pigment material which is readily dispersible in cosmetic compositions and which has improved bulk density and specific surface area characteristics.

Another object of the invention is to provide a new class of cosmetics having richer, more luxurious qualities than have heretofore been obtainable.

It is a further object of this invention to provide improved pigment materials having excellent dispersibility which materials are notable for comprising a wide class of both inorganic and organic pigments pigment extenders and other special, visual-effects materials, and are also notable for enhancing the cosmetic properties of these pigments and pigment materials.

A still further object of the invention relates to providing an improved cosmetic material which enables microspherical powders to be employed in decorative cosmetics without being subject to the drawbacks of known materials.

Additional objects relate to the provision of improved processes for formulating cosmetics and to novel processes for the manufacture of the novel cosmetic ingredient materials of this invention.

Broadly stated, the invention provides novel pigment-material complexes for use in commercial formulations, especially cosmetics, in which a particulate pigment material is chemically coupled to a microsphere material. To simplify the coupling reaction and reduce possible chaining or polymerization, where the pigment material is inorganic, polar or hydrophilic, an organic, non-polar hydrophobic and preferably polymeric microsphere material is used as a carrier for the pigment material. Similarly, hydrophobic organic materials are preferably coupled to inorganic microparticulate carriers, for example by hydroxyl groups on adsorbed water molecules.

However, "homo" complexes in which microspheres are cross-linked are also contemplated as being useful embodiments of the present invention, for example nylon-nylon complexes or silica-silica complexes.

Preferably, the pigment material size is less than that of the microspheres, nearly all the particles of which should have diameters less than 1000 microns, and a number of pigment particles is coupled to each microspherical particle to create what can be thought of as a pincushion effect in which a plurality of smaller pigment particles is chemically bonded or tethered to the surface of a microsphere in a manner providing general coverage of the surface of the microsphere with the pigment particles distributed in a shell-like zone close to the surface of the microsphere particle to which they are attached, like the heads of pins sticking out of a pin cushion. This novel material can be described as a pigment-material-microsphere complex and is an excellent raw material for use in ornamental cosmetics.

In one aspect, the invention provides an improved hydrophobic, dispersible, high-loading cosmetic material with a low surface area-to-volume ratio, low bulk density comprising a pulverized inorganic cosmetic pigment material coating and coupled to from 5 to 35 percent of an organic polymeric microspherical powder of diameter less than 1000 microns by from 1 to 5 percent of a titanate coupling agent wherein the inorganic pigment material is smaller than the organic microspheres and the coupled product has a generally spherical particulate shape, said inorganic cosmetic material and said cosmetic material being capable of being coupled by said titanate coupling agent.

In another aspect the invention provides an pigment-material-microsphere complex of low specific density comprising:

a) microsphere-material particles having a particle size less than 1000 microns;

b) a plurality of pigment-material particles covalently bonded to said polymeric particles; and c) a coupling agent residue extending between said pigment materials and said microsphere particles whereby they are covalently bonded;

one of said microsphere or said pigment materials being an organic material and the other being inorganic and said coupling agent residue being derived from a coupling agent reactive with said microsphere particles and reactive with said pigment material particles.

While some ionic attraction or van der Waal's bonding may be a component of the chemical bonds providing the coupling, it is preferred for the coupling to be by covalent bonding, or electron sharing.

A particularly desirable complex has a substantially uniform layer of pigment particles coupled to each microsphere so as fully to coat it and present the pigment's visual properties more or less substantially uniformly in all directions from the complex particle, in the manner of an outer skin.

Such inventive complexes are useful when incorporated in liquid phase or semi-solid dispersions for manual application by spreading, including make-up, nail enamel eye shadow and the like. The complexes can impart valuable additional properties to appearance-enhancing cosmetics. These properties include not only good appearance and ability to sustain and develop pigments, but also end-product characteristics such as spreadability. Additionally, the novel cosmetic-material complexes of this invention can provide valuable processing advantages in the manufacture of such cosmetic end products, and the invention extends to such improved manufacturing process which use microsphere-complexed pigment materials in place of conventional pigments and the invention further relates to the new cosmetic end-products that result.

DESCRIPTION OF THE PREFERRED EMBODIMENTS

In a preferred embodiment, the invention relates to novel complexes of discrete, particulate cosmetic materials, especially irregularly shaped materials, such as pigments and what may be called pigment materials, which term is often used to include pigment extenders and other materials that modify the characteristics, especially the visual characteristics, of the end product cosmetic, for example, talc, silica, sericites and pearlescents and mica.

Pigments coupled according to the invention are held in a novel spatial distribution which avoids agglomeration and reduces settling and furthermore facilitates dispersion in hydrophobic media. The resultant approximately spherical single-particle layers exhibited by preferred embodiments of the invention provide a very efficient spatial distribution of the pigment with good fill in formulations and excellent display of the pigment's visual properties.

The novel complexed pigment materials of this invention are valuable ingredients when substituted for standard pigments in many cosmetic formulations, to which they bring richness, smoothness and other desirable properties. Of particular interest are: powder make-up compositions, where controlled oil absorption is important so that the make-up does not dry the skin; and aqueous or oil-phase cosmetics where the improved dispersibility of the pigment complexes is valuable.

In a liquid system, improved dispersion may be achieved through reduction of surface area of the material being dispersed, i.e., spherical particles disperse more uniformly than cubic or irregular shaped particles. Improved dispersion also allows higher levels of pigment material to be loaded into the dispersant.

Many diverse coupling agents can be used to provide a bond between the pigment material and the microsphere material. The coupling agent must be capable of bonding So both the pigment material and the microspheres under reaction conditions that will not be deleterious to either ingredient. Preferably, the coupling agent has one functional group that is reactive with the pigment material and a different group that is reactive with the microsphere material. The residual linking group should be inactive or innocuous in cosmetic compositions and in their processing. Preferably also, the coupling agent coats the pigment material to improve its dispersibility without unduly detracting from its pigmenting properties.

In general, organofunctional coupling agents are preferred, especially those with a hydrolyzable moiety that will couple to an inorganic material and a non-hydrolyzable moiety that will couple to an organic material. While the parameters of suitable coupling agents will be discussed more fully below, many suitable agents can be found in the various chemical arts and they include classes of compounds such for example as of organofunctional aluminates, titanates and zirconates as well as organofunctional silanes.

A preferred class of coupling agents comprises titanate coupling agents, and these are effective in coating inorganic pigment materials, giving them a hydrophobic character rendering them more compatible with oily phase dispersants.

The invention relates to the coupling of particulate components of a make-up. An organic particulate material can be coupled with an inorganic particulate material to provide a combination or complex that is a homogeneous, uniform material that resists separation and disperses better than an uncoupled mixture of the same materials.

Microspheres are value-added ingredients in today's formulations. In a preferred embodiment, the invention extends and adapts some of the desirable properties of microspheres to irregularly shaped organic and inorganic pigments, using an isopropyl triisostearoyl titanate to couple pigment materials to microspheres. The new complexed compounds of this invention offer increased applications not achievable by the uncoupled components whether used singly or together.

Microspheres disperse more uniformly than most pigments in both oil and aqueous-based systems and also in emulsions, having the lowest specific surface area per unit volume. Produced to a narrow particle size range, microsphere complexes blend more uniformly in pressed and loose powder systems. The pigment-complexed microsphere materials of this invention have many of these advantages while, depending upon the particular pigment and microsphere material chosen, avoiding many of the drawbacks of employing microsphere materials, especially organic polymeric microsphere materials in cosmetic compositions.

The inventive cosmetic pigment-material-microsphere complexes have markedly improved and useful characteristics for cosmetics including: a low surface area to volume ratio; improved dispersion; improved viscosity and better flow; and uniform reflectivity.

Commercially available microspherical powders useful in the preparation of the cosmetic materials of this invention include organic polymeric materials such as polyethylene, polypropylene and copolymers thereof, polyurethane, polyesters, polyamides, polymethylmethacrylate, nylon, ethylene acrylates copolymers and polyvinylidene copolymers. Substantially any non-toxic, non-irritant, cosmetically compatible organic polymeric material that can be satisfactorily coupled, can be used. Inorganic microsphere powders including, for example., silica, magnesium carbonate, and titanium dioxide can also be used.

Both organic and inorganic microspheres can be solid, porous or hollow or mixtures thereof. Such microspherical powders generally have diameters of less than 1000 microns and preferred powders have diameters of from 1 to 100 microns. Effective results can be obtained with microspheres of from 2 to 50 microns with many useful, commercially available microsphere materials falling in the range of from 2 to 20 microns. Although useful results can be obtained with microspheres having an average size of about 2 microns, larger diameters for better spatial distribution of coupled pigments are preferred.

The characteristics of some commercially available microspherical powders useful in the practice of this invention are set forth in Tables:

TABLE 1

Typical Values of Quantitative Microsphere Properties.

| | Avg. Particle Size microns | Apparent Density g/in$^3$ | Oil Absorption g/100 g | Melting Point °C. |
|---|---|---|---|---|
| Ethylene Acrylates Co-polymer | 5–15 | 2.4 | 60 | 104 |
| Polyethylene | 10 ± 2 | 2.9 | 90 | 109 |
| Nylon I | 5 | 3.9 | 55 | 165–171 |
| Nylon II | 2–20 | — | 90 | — |
| Polymethyl-methacrylate (PMMA) | 2–15 | 5.4 | 60 | N/A |
| Silica | 9 ± 2 | 5.5 | 150 | N/A |
| Polyvinylidene copolymer (PVDC) | 5–35 | 0.2 | 1270 | N/A |
| Polyurethane | 10 | 8.3 | 60 | N/A |

Apparent density is determined on the loose material. Oil absorption is determined by ASTM D281-84. "N/A" is "not applicable".
1 An example of a suitable class of polyvinylidene copolymers is
2 that of acrylo-nitrile vinylidene chloride copolymers.

TABLE 2

Qualitative Microsphere Properties

| | Organic | Inorganic | Solid | Hollow | Porous |
|---|---|---|---|---|---|
| Ethylene Acrylates Copolymer | X | | X | | |
| Polyethylene | X | | X | | |
| Nylon | X | | X | | |
| PMMA | X | | X | | |
| Silica | | X | | | X |
| PVDC | X | | | X | |
| Polyurethane | X | | X | | |

Of particular interest is the PVDC material listed above which comprises hollow microsphere particles and has an exceptionally low apparent or bulk density. Such materials, when complexed according to the methods of this invention, provide a particularly attractive product whose low density imparts a highly desirable bulk density reduction to pigment materials with which they are complexed. Further advantages are desirable characteristics such as richness and smoothness in cosmetic formulations and also high oil-absorption characteristics to the cosmetic. (As noted above, the oil absorption of raw, hollow polymeric microspheres may be excessive.) Hollow microsphere forms of other organic polymers are available and similarly advantageous. Bulk densities below 0.5 g/in$^3$ are available and useful. Such materials are extremely hard to process in their raw state as they become airborne and fly everywhere. Complexing by the method of this invention solves this problem.

Preferred embodiments of the cosmetic materials include pigment materials, both inorganic materials, especially those that are customarily ground before use and also inorganic materials that are sometimes irregularly shaped, in the sense that they are clearly not spherical, are prone to have notably angular surfaces with occlusions and voids between particles and tend to include a wide range of particle sizes within samples. Such features are characteristic of many inorganic pigment materials. Organic pigments tend to be gritty, having sharp angular surfaces. Being small relatively high density particles, they are hard to disperse and to keep in suspension.

Some examples of irregularly shaped organic and inorganic pigment materials that can be used as particulate cosmetic materials to be coupled to microspheres are: boron nitride, D&C red #6 barium lake, D&C Red #7 calcium lake, D&C red #34, FD&C blue #1 aluminum lake, yellow, black and red iron oxide, carmine, ferric ammonium ferrocyanide, ferric ferrocyanide, manganese violet, ultramarine blue, ultramarine violet, ultramarine pin, silica, mica, talc, bismuth oxychloride, titanium dioxide, nylon, flour, starch, complexed metal starches and polyethylene, and metallic powders, including for example, aluminum powder and bronze powder. Clearly such metallic powders will require a choice of process conditions that attaches to the surface of the particles and avoids destroying the body of the particle itself. Pigment materials generally range in size from about 15 nanometers to 10 microns, with coloring pigments not usually exceeding about 2 microns in approximate diameter.

While the lower limit may appear to be extremely small, it should be noted that a commercially available titanium dioxide pigment has an average primary particle size of 21 nm and a specific surface area of about 50m$^2$/g and there are common pigments, such as iron oxide pigments that are known to be smaller. It can readily be appreciated that a substantially continuous shell of such fine-particulate pigment coupled to an organic microsphere of several microns diameter achieves an excellent spatial distribution of the pigment with much improved covering power and apparent bulk density, a quite new material.

In making the present invention, I have discovered that by coupling irregularly shaped or multi-faceted pigment materials to the microspheres described above using for example titanate coupling agents, the coupled pigment products acquire many of the desirable physical characteristics of the microspherical powders while retaining their valuable pigment properties. Importantly, the basic spherical shape of the microspheres is maintained in the coupled material, so that what were in many cases small, irregularly shaped, multi-faceted pigment materials having a tendency to agglomerate are now held in an organized spaced relationship. This spacing improves many of their cosmetic characteristics, especially the coupled pigment materials' dispersibility. Clearly this improvement in dispersibility is more than mere improvements in phase compatibility obtainable by prior art surface treatments, because reductions in bulk density of the rather dense pigment materials which are provided by the present invention, help reduce any tendency of the materials to settle out.

Such irregularly shaped complexed pigment materials can be considered as being distributed around each microsphere particle on generally spherical or spheroidal surfaces or in generally spherical shells, with radii greater than the average pigment particle size, preferably at least two or three times the size. This distribution is illustrated in a general manner in the accompanying micrographs which will be described hereinafter. In this way optimal use of the surface properties of the pigment is obtained. The complexes display similar reflectivity in all directions. In general, these complexes will be much larger in size than any of the cosmetic materials with which they are formulated and will naturally tend to present an evenly pigmented outer surface at any exposed surface. This of course is a highly desirable cosmetic characteristic. The size of the generally spherical complexes provides plenty of room for smaller particles to be accommodated between them. Their sphericity promotes blendability with other cosmetic ingredients.

A further and surprising advantage is displayed by the inventive complexes in that, where adequate pigment material is used in manufacturing the complex, the oil absorption characteristics of hydrophilic polymeric microspheres, especially very absorbent hollow ones, can be significantly reduced. This is important, to avoid undue drying effects of the end product caused by excessive absorption of skin oils.

Thus, the pigment shell or coating on a low-density, organic, polymeric microsphere particle, or core, can protect or modify the properties of that core, while gaining improved spatial distribution leading to isotropic light reflectance, bulk density and specific surface area characteristics for the pigment material. There is a synergistic relationship, the one material gaining properties from the other. Thus, the presence, especially of a hydrophilic or oleophobic pigment coating, can reduce the accessibility of an oleophilic organic core to oils, and thus control oil absorption. In this context, a shell of silica particles can greatly reduce the oil absorbency of organic polymer microspheres, especially if it is a more or less solid or closed shell. Inorganic, unreactive materials such as silica usually have a small quantity of adsorbed water providing available sites for the attachment of hydrophilic moieties.

In some cases, the microspheres may be many times the size of the pigment material, 10, 50 or even 100 times, so long as the size of the resultant pigment-material-microsphere complex particle does not exceed about 1000 micron (1 mm.)

Alterations of the microspheres' qualitative properties may also be made, yielding advantages in the resulting composition or processing of the composition. For example, they may be treated with surfactants to make them more dispersible, of value with silica, or pH-modified by an acid treatment or base-catalyst treatment.

The irregularly shaped coating or pigment materials should be ground, milled or pulverized to a size, preferably between 15 nanometers and 10 microns, in relation to the microspheres, which is such as to enable the material to coat the microspheres and provide a coupled product or complex having a generally spherical shape. Such comminution of the pigment material typically results in particles that have sharp angular faces and that are far from spherical. Organic pigments, in particular, are gritty when comminuted. Complexing with inorganic microspheres improves the bulk texture and blendability of such gritty organic pigments.

It has been discovered that a titanate coupling agent can join an inorganic material to an organic microspherical powder and join organic material to an inorganic microspherical powder. In joining the materials, moisture and air voids on the irregularly shaped material can be eliminated when these materials are coupled to the microsphere, thus tremendously reducing the surface area.

An improved method is to solubilize the titanate coupling agent in a volatile solvent such as isopropyl alcohol, heptane or, preferably, a high-purity, fractionated isoparaffinic solvent, and then mix it with or spray it on the materials to be coupled.

Liquid monalkoxy ($C_1$ to $C_{20}$) isostearoyl titanates, especially isopropyl triisostearoyl titanate, have been found effective as coupling agents in accordance with the invention.

Titanate coupling agents are well known materials and they can be used in a number of different coupling processes that are described in relevant literature, for example a chapter entitled "The Chemistry of Titanate Coupling Agents", pages 2-9 and 26-29 in "Ken-React Reference Manual—Titanate, Zirconate and Aluminate Coupling Agents", Monte et al., and M. Schlossman U.S. Pat. No. 4,877,604.

In general terms, a titanate coupling reaction mechanism is believed to proceed as follows.

A monohydrolyzable group attaches to a proton on the surface of an inorganic pigment material, followed by hydrolysis or solvolysis, and then transesterification and transalkylation, whereupon the water of hydration and air voids on the inorganic pigment surface are replaced by a monomolecular layer of organofunctional titanium, the titanate forming a covalent bond (electron sharing) with a proton on the inorganic surface. The titanium is bonded to oxygen atoms and to the inorganic surface. The coated inorganic material is then able to be joined to a microspherical surface, especially an organic surface, by the coating.

Monte et al. U.S. Pat. No. 4,098,758, the disclosure of which is herein incorporated by reference thereto, describes one class of titanate coupling agents which can be used to couple inorganic pigments to organic polymers and which have the advantage of avoiding multilayer coatings on the pigment. These coupling agents can be used in the practice of the present invention. Furthermore, analogous titanate coupling agents having different proportions of hydrolyzable to non-hydrolyzable groups from those required by Monte, can be used. There is a great diversity of substituents that can be present on the coupling agent. Many of these are set forth in Monte. Such titanate coupling agents can also be used to couple organic pigment materials to an inorganic microsphere carrier.

Clearly other coupling agents can be used with similar effect and advantage, for example, zirconate or aluminate coupling agents such as neopentyl (diallyl) oxyl, tri(dioctyl) phosphito zirconate and equivalent aluminates. However, titanates constitute a preferred species, whose effectiveness and desirability for the purposes of this invention have been demonstrated by experiment, as disclosed herein and are known to cosmetically compatible with few, if any, undesirable side effects. The use of titanium in the form of titanium dioxide is of course a standard practice in the cosmetic arts and its safeness is well established.

A number of surfactants having a polar terminus for attachment to or coating inorganic pigments having a hydrophilic surface, such as those disclosed in Ayala U.S. Pat. No. 4,952,651, can also be used as coupling agents. These surfactant-type coupling agents include, for example, triols, especially trimethylol ethane and propane and dimethyl polysiloxanes. Ayala's surfactants have, in addition to a reactive polar terminus capable of attachment to active sites on hydrophilic pigment particles, a non-polar terminus for compatibility with a non-polar matrix such as a polyolefin. While such agents could be used in the practice of the present invention to complex polar and non-polar particles, and can be effective for example where the polar terminus comprises an extensive alkyl or alkyl-substituted ligand that binds to polymer microspheres reasonably well by van der Waal's forces, it is preferred that the non-polar terminus be reactive and be capable of being chemically covalently bound to an organic microsphere without disturbing the bonding to the pigment.

In summary, a coupling agent for coupling polar particles having active sites to non-polar particles can have the general formula:

$$X_n(M)Y_m$$

where M is a carrier moiety with a valency state of from 2 to 6, preferably from 2 to 4; n and m is each from 1 to 5 with n+m equaling said valency state; X is a polar-reactive ligand reactable with said active sites on said polar particles and Y is a non-polar-reactive ligand reactable with said non-polar particles.

M can be selected from the group consisting of metallo moieties including titano, zircono and alumino, phosphato or phosphito moieties, secondary, tertiary or quaternary substituted ammonium moieties and bi-, tri- or quadri-functional organic groups, including aliphatic, cyclic, heterocyclic and polycyclic organic moieties.

X preferably includes a hydroxyl or alkoxy moiety of from one to five carbon atoms and is hydrolyzable, but other polar-binding ligands can be used.

Y can be any ligand which will couple to the desired non-polar particle, be it pigment material or microsphere without interfering with the X-bond to the polar particle. Examples of suitable Y ligands include alkoxy groups having from 1 to 24 carbon atoms, such as stearoyl, oleyl, and palmitoyl, straight, branched chain and cyclic homologues there of, either saturated or unsaturated, and substituted homologues thereof with halo, amino or nitro substituents.

Thus, in general terms, a preferred class of coupling agents comprises a monohydrolyzable ligand for attachment to inorganic pigment materials by hydrolysis, a metallo carrier moiety and an organofunctional ligand or ligands for attachment to the organic polymeric microspheres. Conveniently, the organofunctional ligand can comprise an ester-like moiety that can attach to paraffinic chains or groups in the polymeric microspheres by trans-esterification and trans-alkylation.

Many other variants of M, X and Y that can serve the general purposes of this invention will be apparent to those skilled in the art from the disclosure herein and from the literature cited herein, as well as from other literature known to those skilled in the art. Isopropyl triisostearoyl titanate, the preferred coupling agent used herein, exemplifies the formula above. Another class of possible coupling agents, not discussed above, comprises organofunctional silanes, especially those possessing both organic and inorganic reactivity, (the possession of which is a feature of preferred coupling agents) for example, Dow Corning Z-6020 silane which is designated N-(beta-aminoethyl)-gamma-aminopropyl-trimethoxysilane of formula $(CH_3O)_3$-$Si(CH_2)_3NH(CH_2)_2NH_2$. Notable are the aminoalkyl organic group and the trimethoxy silyl inorganic group which can serve as coupling moieties in a variety of coupling agents. Other usable silanes include amine, epoxy, vinyl, chloralkylamine and vinylbenzylamine homologs of the above Z-6020 silane.

Preferably, the coupling agent is chosen to favor the coupling of a number of pigment particles to a single microsphere without chaining or layering of the coupling agent. Depending upon their relative particle sizes, this number is preferably at least four and even at the outer limits of relative proportions is probably not in excess of a thousand, while 100 is a more practical maximum. An optically continuous layer of pigment particles is desirable.

It is also preferred that the coupling agent be capable of coating inorganic pigment particles having a hydrophilic surface to render that surface hydrophobic and the particles dispersible. Using such a coupling agent and appropriate process conditions, a pigment-material-microsphere complex can be produced which presents hydrophobic, non-polar surfaces regardless of the character of the inorganic pigment coating the complex; which has isotropic reflectivity displaying the optical character of the pigment material; which is dispersible in oils and has desirable density and specific surface area characteristics. Isopropyl triisostearoyl titanate and other organotitanates are examples of such microsphere-coupling materials that can also coat inorganic pigment particles.

In a preferred embodiment, the organofunctional group or groups, and there can be three such groups per titanium atom, are alkoxy groups, giving the coated inorganic pigment material a hydrophobic or lipophilic surface. As disclosed and claimed by M. Schlossman, such pigment materials have improved dispersibility in cosmetic formulations and, by virtue of their titanate coating, provide surprising advantages both to the processor and the end user. These advantages perhaps can be attributed to the surface characteristics of the titanate-coated particles which, in addition to being hydrophobic, are less likely to trap air and moisture between the particles.

The present invention achieves some surprising advantages over the prior art, including M. Schlossman, by improving the spatial distribution of particulate cosmetic materials. This distribution is obtained by chemically bonding or coupling the particulate cosmetic materials to a microspherical carrier. One way of doing this is by coupling coated particles, such as those described above, to organic polymeric microspheres using per se known reaction techniques.

As a practical matter, using bifunctional coupling agents, for example organic titanates having hydrophilic and hydrophobic reactive groups, the coupling process can be effected in a single step. In such a one-step process, the particulate cosmetic material, the microspheres and the coupling agent are mixed under conditions promoting the desired coupling reactions, for example by spraying or otherwise mixing a solution of the coupling agent with a mixture of the other two ingredients, which can be a dry mix in a blender, and drying off the solvent with heat, while mixing or blending. In preferred embodiments, the coupling agent or titanate is substantially fully reacted to the particulate cosmetic material surface by the heat required to dry off the solvent.

A titanate coupling agent dissolved in an organic solvent, for example, an isopropyl triisostearoyl titanate coupling agent, will partially react at room temperature, but an elevated temperature, for example in the range of from 80° to 300° C. is preferred to effect coupling. The solvent can then be removed in a drying step which usually completes the coupling reaction steps of hydrolysis, transesterification and transalkylation.

A volatile organic solvent with, for example, a distillation range between 97°–140° C., is preferred for use in the coupling process, especially where the coupling agent is a liquid monoalkoxy titanate, especially an alkyl trialkoyl titanate.

A particularly suitable solvent is an isoparaffinic solvent such as Isopar C (trade mark) manufactured by the Exxon Corporation. This has a narrow distillation range of from 98° to 106° C., has exceptional purity of isoparaffinics with low limits of other hydrocarbons and of trace impurities. Isoparaffinic solvents have similarities to heptane, which could also be used, but have a lower heat of vaporization, a mild odor add are relatively inert. Their freedom from essentially any polar compounds is of particular value in carrying out the present invention as is their low toxicity. Furthermore, Isopar C has been found to yield better coatings than other solvents, for example isopropyl alcohol.

The solvent can be added to the coupling agent or titanate to comprise between 1–99 percent of the formula. A good blend has between 5–50 percent solvent, and a preferred ratio between 15–35 percent by weight. In practicing the coupling process of this invention, the powdery ingredients, namely the particulate cosmetic or pigment material and the microspheres can be charged to a vessel provided with a vacuum system capable of removing volatile solvents.

Preferably the solvent is recovered and examined for purity. In a well-controlled process with adequate ventilation it can be recycled. Preferably the recovered solvent should not contain any titanium. This provides a further quality control check and also confirms binding of the coupling agent to the particulates.

When coupling an organic polymer to pigment or extender pigment, the organic polymer may comprise as little as 15 percent by weight or less of the mixture and the titanate can be present in amounts of at least 0.01 percent by weight, although from about 1 to 5 percent by weight is more practical. Preferred compositions use the microspheres in the amount of 5 to 35 percent by weight and a coupling agent, for example, isopropyl triisostearoyl titanate in amounts of 1 to 3 percent by weight. In general, however, the weight of microspheres will be from 5 to 100 percent of the weight of pigment material.

A particularly preferred embodiment of the invention employs hydrophilic-surfaced inorganic pigment materials coupled to organic polymeric microspheres.

Specific advantages of preferred pigment-material-microsphere complexes of this invention include: improved hydrophobicity; a higher melting point; more uniform specific gravity and bulk density; improved dispersibility; lower viscosities at comparable use levels; higher solids loading is possible; improved adhesion; smoother texture; unique surface area characteristics and reduced processing times and clean up is necessary.

Such coupled microspherical powders and fillers are useful in cosmetic compositions, especially oil-based and aqueous-based emulsions and poured powders. The advantages include: uniform specific gravity; a controlled oil absorption rate; lower specific surface area is achieved; maximum solid content for a given viscosity is achieved; minimum viscosity for a desired solids load is achieved; improved flowability and ease of dispersion; improved spreadability and application; a unique surface texture (smooth/creamy) is achieved; and spherical particulate characteristics are maintained during processing. Organic polymeric microsphere materials can thus be used to better incorporate pigments and fillers, or extender pigments, into a cosmetic.

These materials also yield advantages when incorporated into pressed powders. The powders are easier to press; the oil absorption rate is better controlled; packing is reduced; adhesion is improved; density is uniform; and a smooth surface is achieved.

The polymer microspheres used in cosmetics such as polyethylene may begin to soften at 95° C. to 110° C. and then deform or melt and flow. It is not unusual for these temperatures to be realized and exceeded in the processing of cosmetics.

By treating polymer microspheres mixed with an inorganic material such as boron nitride with a titanate or other type of coupling agent, insulated microspheres are achieved. The coating acts as insulation preventing the melting or deforming of the microspheres during processing. Thus, the dispersion advantages etc., due to microspherical shape are available in the final cosmetic product.

In accordance with the inventive method of making an improved cosmetic component, one selects an organic microspherical material for cosmetic use. A pulverized inorganic material to be coupled to and carried by the organic microspherical material is combined with the microspherical material and the inorganic material to form a mixture. The liquid titanate coupling agent is added to the mixture and the resulting mixture is thoroughly mixed to form a mixture of microspherical compounds of inorganic material coupled to organic microspheres by the titanate coupling agent. Tests on specific coupled combinations have been performed and scanning electron microscope images have been made for components, mixtures and coupled mixtures.

Polyvinylidene copolymer (PVDC) microspheres have been combined with talc, with black iron oxide and with spherical silica. Isopropyl triisostearoyl titanate was used as a coupling agent. Polyethylene was coupled with boron nitride using isopropyl triisostearoyl titanate. The amount of isopropyl triisostearoyl titanate was 2 percent by weight in all cases.

Talc was mixed with PVDC in a 85 to 15 ratio. The specific surface area of the mixture was 5.2 meters$^2$/gram, talc alone has a specific surface area of 8.0 meters$^2$/gram. When the mixture was treated, the specific surface area was reduced to 0.57 meters$^2$/gram.

A 20 percent composition of the treated talc-PVDC mixture in mineral oil was pourable with a measurable viscosity while a like composition using an untreated mixture formed a paste and had no flow property.

It was found that one gram of the treated material would float on 50 ml of water for more than an hour. This was not the situation without treatment. The treated mixture thus exhibits greatly increased hydrophobicity.

When PVDC and silica were combined in a 15 to 85 ratio and treated with isopropyl triisostearoyl titanate, a float time for one gram of material on the surface of water was also in excess of one hour. When an untreated mixture was floated on water, the silica swiftly separated out and sank.

Polyethylene microspheres having a melt range of 105° to 106° C. were combined in a 50 to 50 ratio with boron nitride powder and treated with isopropyl triisostearoyl titanate. Again, the titanate amount was two percent by weight of the mixture. The melt range for the treated microspherical mixture was increased to more than 140° C.

Some preferred embodiments of the invention will now be described, by way of illustration, and without limitation, as the scope of the invention is limited only by the appended claims, with reference to the following examples, in which parts are by weight.

EXAMPLE 1

30 parts of nylon II, as described in Table 1, and 70 parts of mica were intimately blended in a vacuum blender for 5 minutes with mica ground to an average particle size of 5 microns and a specific surface area of 1.4–1.6 meters squared/gram. Sufficient 34 percent solution of isopropyl triisostearoyl titanate in Isopar C (Exxon Corporation) was sprayed onto the surface of the blended powders to coat the powder with about 2 percent by weight of isopropyl titanium triisostearate. The blender temperature was set at 80° C. and the powdered complex reaction product was dried for 1 hour. After a five minute post-process blend, and cooling, the powder was discharged from the blender.

The nylon-mica complex reaction product of treated powder has a slightly waxy odor, good slip, good adhesion to the skin, is hydrophobic and exhibits significantly reduced oil absorption (40 grams oil/100 grams) than the base uncomplexed nylon II particles. In addition, the composite powder or complex can easily be dispersed in water, like the mica, and unlike the nylon, so that the complex or composite powder acquires useful characteristics from both its parent powders.

The recovered solvent is analyzed and has a boiling point elevated by 2° C. compared with Isopar C. This difference is acceptable. The percentage of titanate bound in the composite powder product was determined to be 2 percent. No solvent odor could be detected in the product.

Evidence of the coupling treatment and its effects was also determined by resistivity measurements by applying a voltage between metal electrodes in a dry contained of powder, the powder being lightly tapped to make contact at the electrodes. Various nylon microsphere materials exhibited high individual resistivities of insulative value in excess of $10^{14}$ ohm-cm. Mica alone showed a semiconductive resistivity value of about $1.5 \times 10^8$ ohm-cm. A 30/70 nylon/mica had a higher resistivity of about $6.6 \times 10^{10}$ ohm-cm. while that of the reaction product complex of Example 1 was about $1.1 \times 10^{13}$, only about one order of magnitude less than the naked nylon microspheres. Interpreting a higher resistance to imply greater hydrophobicity, the complexing process has increased the hydrophobicity of the complex, as compared with the mix, by more than two orders of magnitude, clearly demonstrating coupling.

EXAMPLE 2

15 parts of polyvinylidene copolymer (PVDC) as described in Table 1 were added to a vacuum blender followed by 85 parts of talc pigment. The powders were intimately blended for 5 minutes. A 17 percent solution of isopropyl triisostearoyl titanate in Isopar C (Exxon Corp.) was sprayed onto the surface of the powder mix. The blender temperature was set to 80° C. and the powders were dried for 1 hour. After cooling, the treated powder was discharged to a drum and examined. The composite powder product was hydrophobic, had a slightly waxy odor, had good slip, improved adhesion, and lower oil absorption (180 grams oil/100 grams than untreated PVDC. The PVDC powder used was hollow and very lightweight, being easily airborne. The treated material complex product or composite powder is substantially denser having an apparent density of approximately 1 gram per cubic inch, and could readily be dispensed without becoming airborne. The composite pigment material contained 2 percent isopropyl triisostearoyl titanate by weight had a generally spherical shape, there was no odor of solvent detected and the specific surface area was in the range of from 0.5 to 2 $m^2/g$.

EXAMPLE 3

15 parts PVDC as described in Table 1 and 85 parts mica pigment material were intimately blended in a vacuum blender. The mica had been ground to an average particle size of 5 microns and had a surface area between 1.4–1.6 meters squared per gram. The powder was blended, treated, and dried as described in Example 2. The treated pigment was spherical. The treated pigment had good slip, improved adhesion, was hydrophobic, and had lower oil absorption (180 grams oil/100 grams). The solvent odor could not be detected. The amount of titanate employed was 2 percent by weight of the composition.

EXAMPLE 4

15 parts polyvinylidene copolymer (PVDC) microspheres and 85 parts of silica as described in Table 1 were intimately blended, treated and dried as described in Example 2. The microspheres are extremely lightweight and easily airborne. In contrast, the coupled powder can be easily dispensed. The apparent density of the complexed pigment material is approximately 1.4 grams/cbi. The oil absorption of the PVDC microspheres decreased to approximately 280 grams oil/100 grams. The complexed pigment material is hydrophobic, has good slip, improved adhesion, and a slightly waxy odor. There was no odor of solvent present. The amount of titanate used was 2 percent by weight. The spherical shapes were maintained.

The pigment-material-microsphere complex products of Examples 2, 3 and 4 all had a spherical appearance under a scanning electron microscope, an average particle size of about 20 micron with 90 percent of particles falling within the range of from 5 to 35 micron, and a waxy odor. Talc-, mica- and silica-PVDC complexes produced by methods generally equivalent to those of Examples 2–4 can be advantageously incorporated in anhydrous blushers, shadows, lip powders, eye pencils and lip pencils, and pressed powders. In liquid foundations such complexes are also effective, silica-PVDC complexes being especially so. The latter can also be used, with advantage in solvent or aqueous-based mascara.

In such formulations, customary proportions of pigment are used, although because of the benefits of the invention, smaller amounts may be adequate. Richer, creamier or smoother products can result with better pigment-related appearance qualities.

EXAMPLE 5

15 parts PVDC as described in Table 1 and 85 parts black iron oxide pigment were intimately mixed. The black iron oxide had been ground to an average particle size between 2–5 microns. The mixed powders were blended, treated, and dried as described in Example 2.

The spherical shape was maintained. The treated pigment has good slip, improved adhesion and texture. The amount of titanate was 2 percent by weight. There was no odor of solvent. The treated pigment was hydrophobic.

EXAMPLE 6

5 parts PVDC and 95 parts talc were intimately blended, treated, and dried as described in Example 2. The treated powder was spherical, hydrophobic, had good slip and improved adhesion. The amount of titanate was 2 percent by weight of the composition. There was no odor noticed. The complexed pigment could be more readily pressed than polyvinylidene copolymer.

EXAMPLE 7

50 parts polyethylene as defined in Table 1 were intimately mixed with 50 parts of boron nitride. 99 percent of the boron nitride particles had a particle size below 10 microns. The pigments were blended, treated, and dried as described in Example 2. The complexed pigment had good slip, improved adhesion, and was hydrophobic. The melting point of the complex was increased to about 140 centigrade. Boron nitride is believed to provide insulation to the polyethylene. The pigment complex is particularly useful for incorporation as part of a pressed powder blend. This blend can be pulverized without the polyethylene component melting. The amount of titanate was 2 percent. There was no odor of solvent in the product.

BRIEF DESCRIPTION OF THE DRAWINGS

The following scanning electron microscope photographs depict various microspheres, microsphere-irregular particulate mixtures and microspheres coupled with irregular particulates by isopropyl triisostearoyl titanate.

Photographs 1 to 8 show the shape of the particulate materials to be coupled and photographs 9, 10 and 11 depict the non-homogeneity and uneven distribution of materials in a non-coupled mixture. Such inhomogeneity leads to uneven dispersion, accelerated separation and other problems. Photographs 12 to 27 show the coupled mixtures and the spherical nature of the microspheres remaining intact after being coated with the irregularly shaped material. The materials depicted and the magnification employed in the photomicrographs are detailed in the legends accompanying each of photographs 1–27. Scales in microns are also shown for approximate determination of actual particle size characteristics directly from the photographs. Scanning electron micrographs or photographs 28 and 29 show 70% mica coupled to microspherical ethylene/acrylates copolymer using an organofunctional silane coupling agent at magnifications of 500 and 6,000 respectively.

Figure 1:
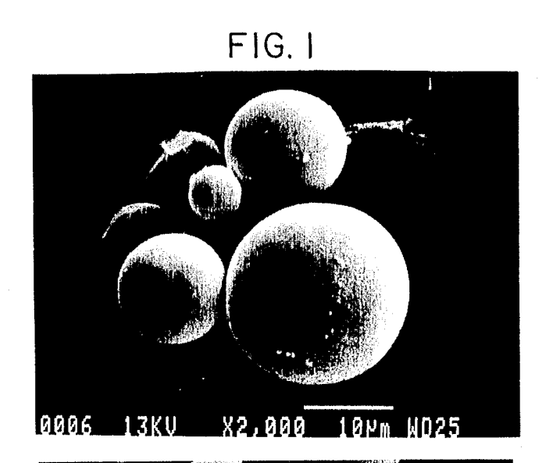
Figure 2:
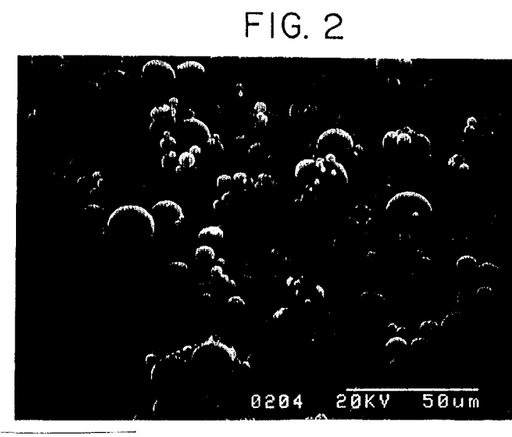
Figure 3:
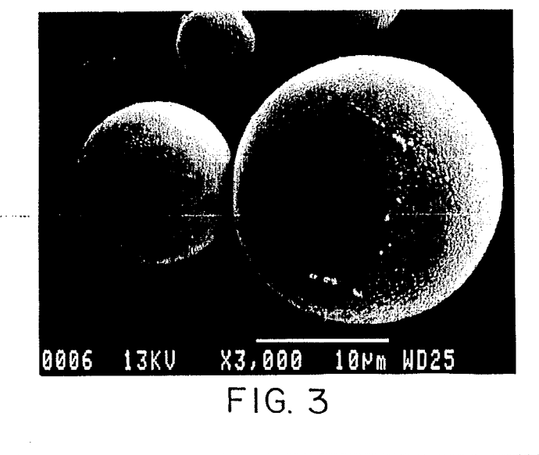
Figure 4:
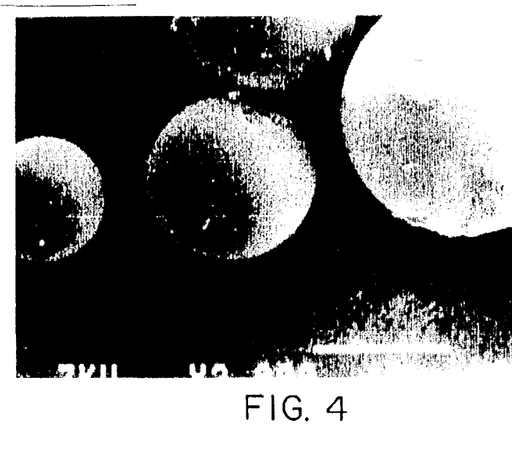
Figure 9:
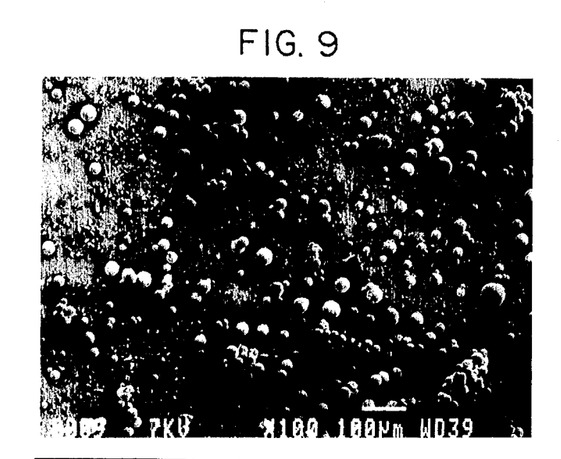
Figure 10:
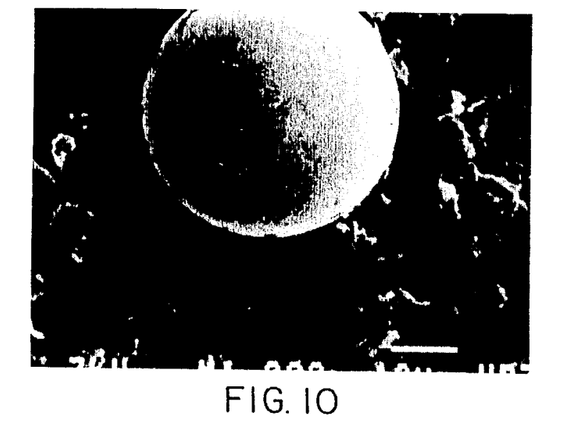
Figure 11:
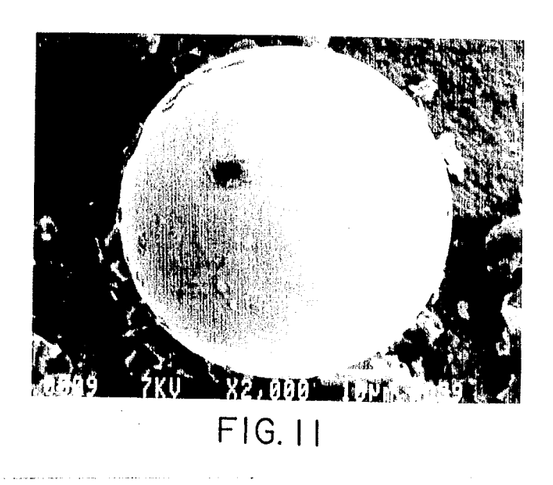
Figure 12:
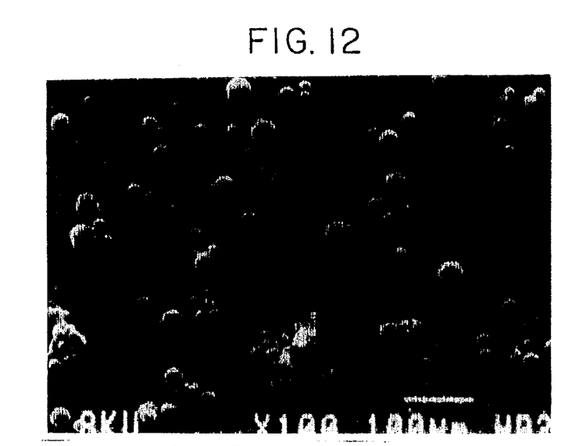
Figure 13:
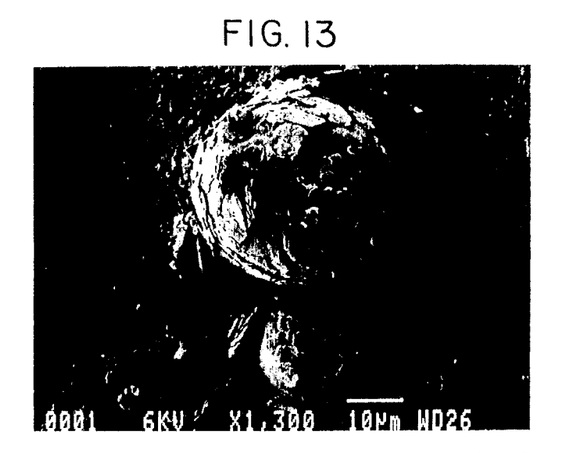
Figure 14:
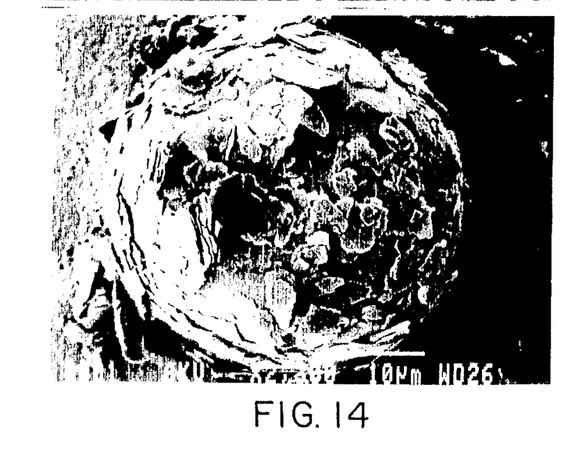
Figure 15:
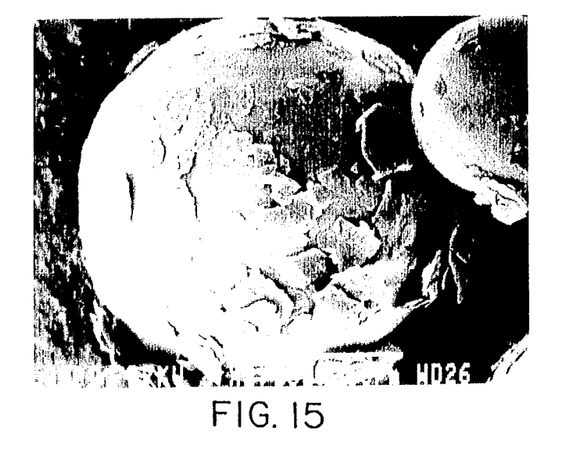
Figure 16:
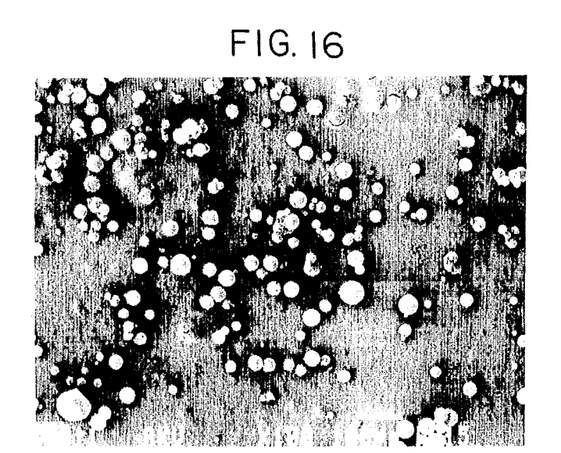
Figure 17:
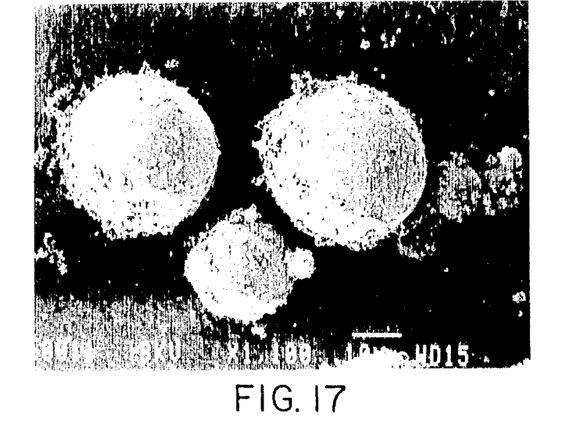
Figure 18:
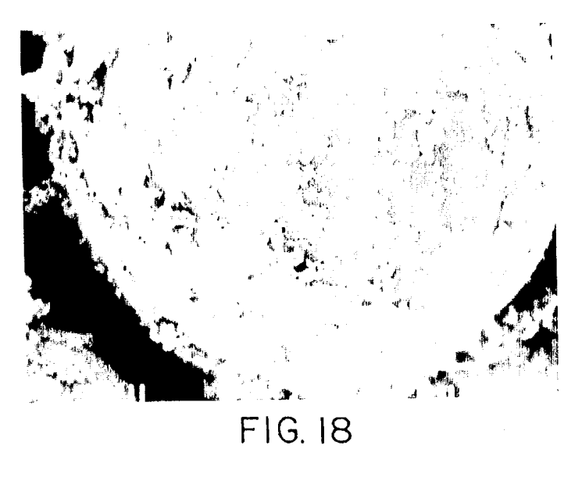
Figure 19:
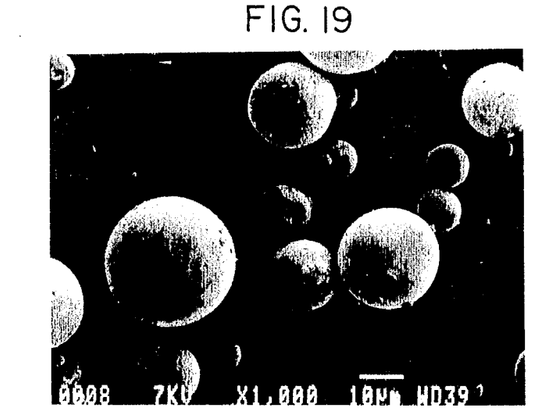
Figure 20:
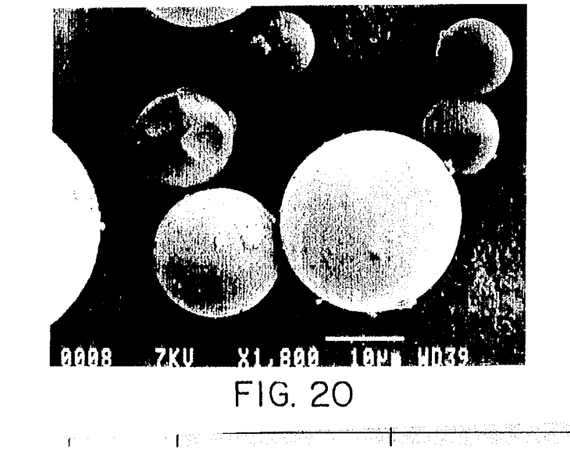
Figure 21:
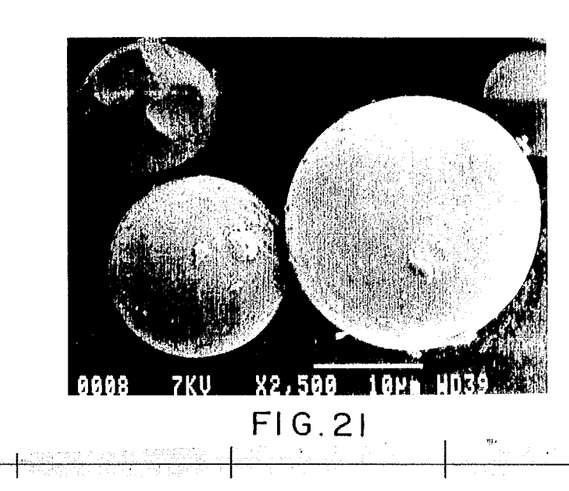
Figure 22:
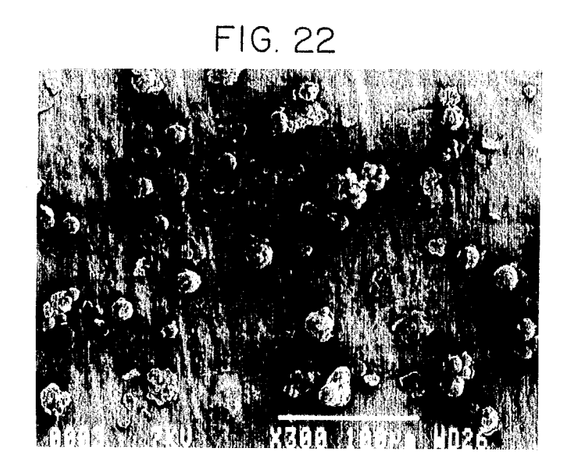
Figure 23:
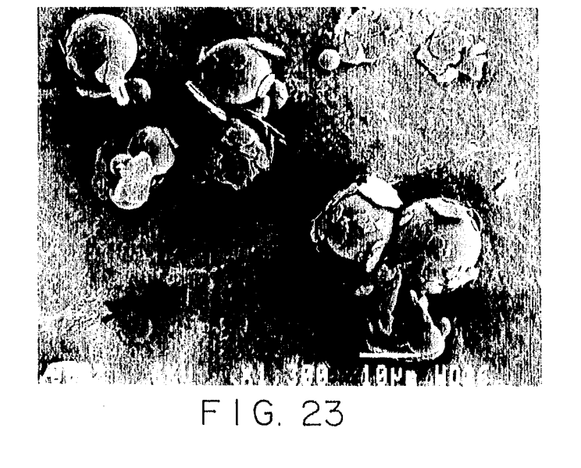
Figure 24:
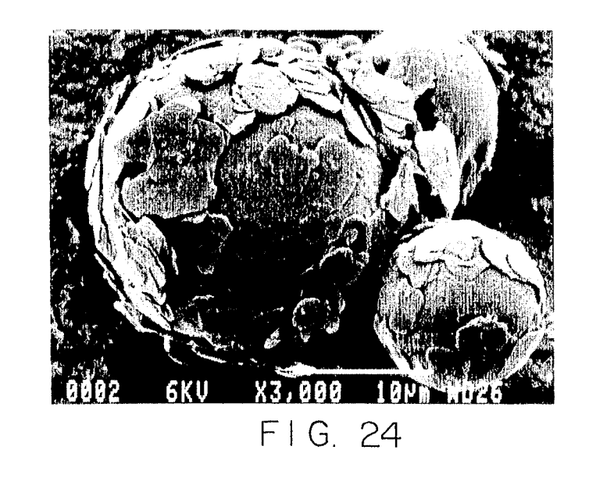
Figure 25:
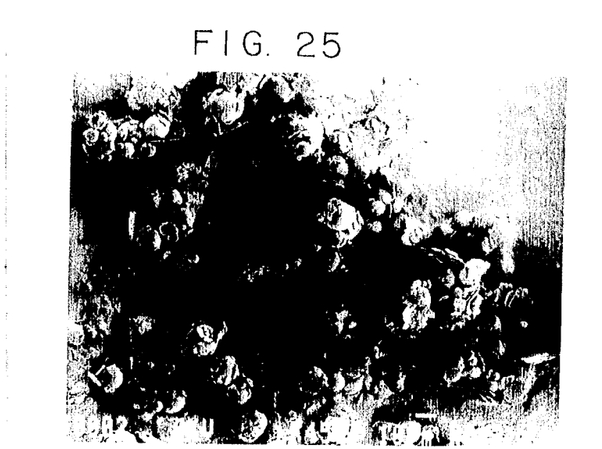
Figure 26:
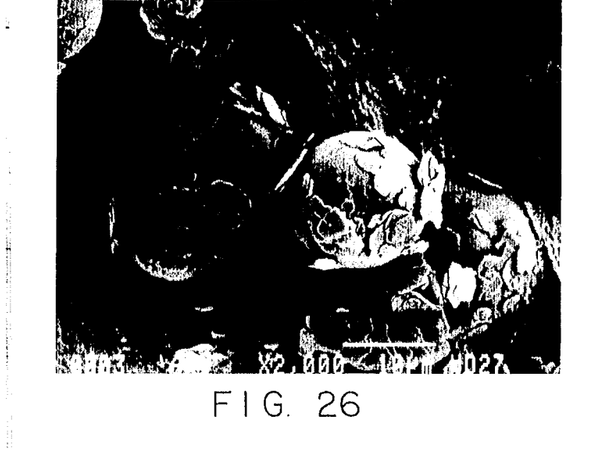
Figure 27:
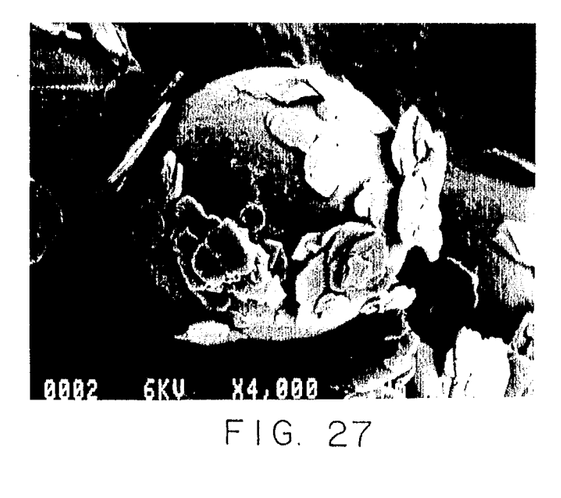
Figure 28:
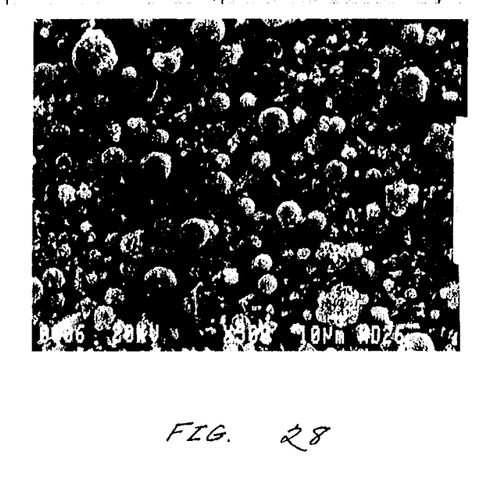
Figure 29:
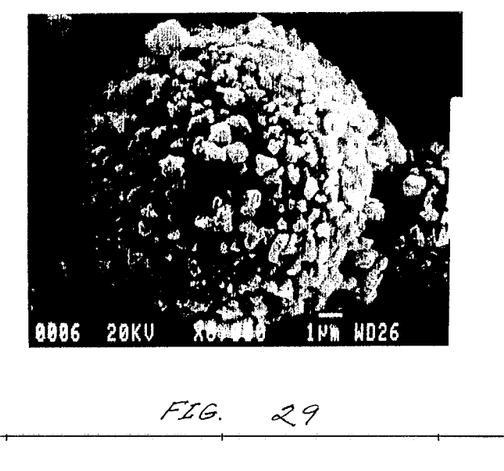

The inorganic materials are much denser than the organic polymers and therefore significant loading in terms of weight of the inorganic material is achievable while maintaining the spherical shape of the coupled materials.

The invention has been described with special reference to the field of cosmetics where it provides outstanding benefits, as set forth herein. It will be clear, however, to workers in other fields that some of the unique benefits of the pigment-material-microsphere complexes of this invention are transferable to and realizable in other fields. For example, in compounding moldable plastics or rubbers, good dispersibility of pigment materials is desirable and the unique three-dimensional control of spatial distribution that is afforded by the microsphere-complexed pigment materials of this invention is also valuable in those fields. Such control affords the prospect of better utilization of pigment materials exploiting the advantages described herein. Accordingly, the invention extends to plastics and rubber materials, cured and uncured, molded and amorphous, as well as paints, inks and artists' materials which incorporate novel pigment-material-microsphere complexes such as those described hereinabove in a manner equivalent to the cosmetic materials described herein.

While an illustrative embodiment of the invention has been described above, it is, of course, understood that various modifications will be apparent to those of ordinary skill in the art. Such modifications are within the spirit and scope of the invention, which is limited and defined only by the appended claims.

I claim:

1. An improved cosmetic compound consisting essentially of a pigment material and microsphere complex of bulk density less than said pigment material's bulk density, said microsphere complex comprising:
   a) microsphere-material particles having an average particle size less than 1000 microns;
   b) a plurality of organic or inorganic pigment particles covalently bonded to each said microsphere particle; and
   c) a coupling agent residue extending between said pigment particles and each said microsphere particle whereby said pigment particles are covalently bonded to said microsphere particles;

one of said microsphere or said pigment materials being an organic material and the other being inorganic, and said coupling agent residue being derived from a coupling agent reactive with said microsphere particles and reactive with said pigment material particles.

2. A cosmetic compound according to claim 1, said compound having a surface area-to-volume ratio lower than a corresponding mixture of said pigment and microsphere materials, wherein said microsphere material particles comprise from 5 to 35 weight percent of an organic polymeric microspherical powder, said pigment material comprises a pulverized inorganic cosmetic pigment material of particles smaller than said organic polymeric microsphere material and wherein said coupling agent from which said coupling agent residue is derived comprises from 1 to 5 weight percent of a titanate coupling agent, said coupled product having a generally spherical particulate shape, said inorganic cosmetic material and said cosmetic material being capable of being coupled by said titanate coupling agent and said weight percentages being based on the weight of said cosmetic compound.

3. An improved cosmetic material according to claim 2 wherein said organic polymeric material is selected from the group consisting of microspherical polyethylene, polymethyl methacrylate, nylon, ethylene acrylates copolymer, polyurethane and polyvinylidene copolymers.

4. An improved cosmetic compound as claimed in claim 2, wherein said inorganic cosmetic pigment material is a cosmetically acceptable insulating material.

5. An improved cosmetic compound as claimed in claim 4, wherein said cosmetically acceptable insulating material is boron nitride.

6. An improved cosmetic compound as claimed in claim 2, wherein said titanate coupling agent is a liquid monalkoxy ($C_1$ to $C_{20}$) isostearoyl titanate.

7. An improved cosmetic compound as claimed in claim 6, wherein said liquid titanate coupling agent is isopropyl triisostearoyl titanate.

8. An improved cosmetic compound as claimed in claim 2, wherein said pigment material is selected from the group consisting of inorganic pigments, pigment extenders, talc, sericites, silica and mica.

9. A pigment-material-microsphere complex according to claim 1 wherein said pigment material particles are polar particles having active sites, said microsphere particles are non-polar and said coupling agent is adapted for coupling polar particles having active sites to non-polar particles and has the general formula:

$$X_n(M)Y_m$$

where M is a carrier moiety with a valency state of from 2 to 6, preferably from 2 to 4; n and m is each from 1 to 5 with n+m equaling said valency state; X is a polar-reactive ligand reactable with said active sites on said polar particles and Y is a non-polar-reactive ligand reactable with said non-polar particles.

10. A pigment-material-microsphere complex according to claim 9 wherein a residue of said coupling agent coats said inorganic pigment material particles.

11. A method of making an improved pigment material of reduced specific surface area said material being a pigment-material-microsphere complex having a specific surface area less than that of a respective uncomplexed pigment material said method comprising the steps of:
   a) selecting a microsphere material to serve as a carrier for said pigment;
   b) pulverizing or obtaining a pulverized pigment material to be carried by said microsphere material;
   c) combining said microsphere material and said pigment material to form a mixture;
   d) adding a coupling agent to the mixture, said coupling agent having a first ligand reactive with said microsphere particles and a second ligand reactive with said pigment material particles;
   e) thoroughly mixing said microsphere material, said pigment material and said coupling agent under conditions to couple said pigment material to said microspheres by reaction of said first and second ligands; and
   f) recovering said pigment-material-microsphere complex from the product of e).

12. A method according to claim 11 wherein said microsphere material comprises organic polymeric microspheres and said pigment material is inorganic.

13. A method according to claim 11 wherein said microsphere material is inorganic and said pigment material is organic.

14. A method according to claim 11 wherein said coupling agent is an organofunctional liquid titanate.

15. A method according to claim 11 wherein said coupling agent is an organofunctional silane.

16. A method according to claim 11 comprising the steps of spraying said coupling agent in solution on said mixture of microspherical and pigment material.

17. A method according to claim 14 wherein said liquid titanate coupling agent is dissolved in an isoparaffinic solvent having a distillation range substantially between 97° and 140° C.

18. A method according to claim 14 wherein said microsphere material comprises from 5 to 100 percent of the weight of the pigment material and said coupling agent comprises from 0.01 to 5 weight percent.

19. A method according to claim 14 wherein said microsphere material comprises from 15 to 35 percent of the weight of the pigment material and said coupling agent comprises from 1.0 to 5 weight percent.

20. An improved cosmetic compound consisting essentially of a microsphere-to-microsphere material complex said complex having a specific surface area less than that of corresponding uncomplexed microsphere material and comprising individual complex particles having multiple microspheres of average particle size less than 1000 microns covalently bonded to a single microsphere by means of a coupling agent residue extending between each said multiple microsphere and each said single microsphere and said coupling agent residue being derived from a coupling agent reactive with said microsphere particles.

* * * * *